United States Patent [19]

Orr, Jr. et al.

[11] Patent Number: 4,872,353
[45] Date of Patent: Oct. 10, 1989

[54] AUTOMATIC SAMPLE FEEDER FOR SUSPENDED SAMPLES

[75] Inventors: Clyde Orr, Jr., Dunwoody; Ronnie Camp, Duluth, both of Ga.

[73] Assignee: Micromeritics Instrument Corp., Norcross, Ga.

[21] Appl. No.: 157,705

[22] Filed: Feb. 19, 1988

Related U.S. Application Data

[63] Continuation-in-part of Ser. No. 125,395, Nov. 25, 1987.

[51] Int. Cl.⁴ ............................................. G01N 35/00
[52] U.S. Cl. .............................. 73/864.85; 73/863.01; 422/64; 366/140
[58] Field of Search ................ 73/863, 863.01, 864.13, 73/864.81, 864.85; 422/64, 65; 366/140

[56] References Cited

U.S. PATENT DOCUMENTS

| | | | |
|---|---|---|---|
| 2,843,169 | 7/1958 | Stein | 366/140 X |
| 3,547,781 | 12/1970 | Guigan et al. | 141/129 X |
| 3,607,097 | 9/1971 | Auphan et al. | 356/39 X |
| 3,607,099 | 9/1971 | Scordato et al. | 73/64.1 X |
| 3,614,434 | 10/1971 | Horwitz et al. | 422/64 X |
| 3,787,185 | 1/1974 | Rohrbaugh et al. | 422/64 |
| 3,790,346 | 2/1974 | Ritchie | 422/64 |
| 3,802,782 | 4/1974 | Natelson | 422/65 X |
| 3,814,582 | 6/1974 | Rohrbaugh et al. | 422/64 X |
| 3,841,835 | 10/1974 | Kishimoto et al. | 141/329 X |
| 3,850,040 | 11/1974 | Orr, Jr. et al. | 73/38 X |
| 3,916,692 | 11/1975 | Abrahams et al. | |
| 3,918,913 | 11/1975 | Stevenson et al. | 141/130 X |
| 3,975,946 | 8/1976 | Ball et al. | 73/61.1 C |
| 4,010,369 | 3/1977 | Daellenbach et al. | 250/308 X |
| 4,059,009 | 11/1977 | Ball et al. | 73/61.1 C |
| 4,094,195 | 6/1978 | Friswell et al. | 277/117 X |
| 4,094,196 | 6/1978 | Friswell . | |
| 4,305,291 | 12/1981 | Nelson . | |
| 4,377,880 | 3/1983 | Jackson et al. | 73/864.24 X |
| 4,450,723 | 5/1984 | Scott . | |
| 4,478,095 | 10/1984 | Bradley et al. | 73/864.21 |
| 4,528,158 | 7/1985 | Gilles et al. | 73/864.22 X |
| 4,566,326 | 1/1986 | Lowell | 73/38 X |
| 4,620,452 | 11/1986 | Seki | 73/864.21 |
| 4,622,457 | 11/1986 | Bradley et al. | 235/464 |

FOREIGN PATENT DOCUMENTS

2850426 10/1979 Fed. Rep. of Germany ........ 422/64

OTHER PUBLICATIONS

Hewlett Packard brochure, "The HP 1090 Series M. Liquid Chromatographs", 10/85, publ. No. 12-59-54-0845, pp. 1-28.

Metrohm advertisement, "Polarography with Metrohm Sheds More Light on Trace Analysis," American Laboratory, Oct. 1987, p. 101.

P.S. Analytical brochure, "Large Volume Autosampler/Fraction Collector for Automatic Systems," FSM 1435/7, pp. 1-2, pub. by Jul. 1988.

Holl, "A System for Producing Reproducible Disper-

(List continued on next page.)

Primary Examiner—Tom Noland
Attorney, Agent, or Firm—Jones, Askew & Lunsford

[57] ABSTRACT

An automatic sample feeder system for handling suspended samples is disclosed, and is particularly useful in connection with a sedimentation particle size analyzer. The system is capable of dispersing a particulate sample into suspension without preliminary sample preparation, maintaining a sample in suspension at the time of delivery of the sample to an analyzer, consistently delivering an acceptable concentration of a suspended sample, and cleaning and flushing its components between samples to avoid contamination. In the disclosed embodiment, sample beakers are arrayed on a rotatable tray, and a sample preparation and delivery assembly consisting of an ultrasonic probe, a stirrer blade, and a dip tube are indexed into position over the beakers in a preprogrammed sequence, and lowered into the beaker for preparation and withdrawal of the sample. The components are rinsed by directing clear liquid back through the dip tube onto the rotating stirrer blade, scattering the liquid.

16 Claims, 5 Drawing Sheets

OTHER PUBLICATIONS sions of Particles in Liquids", 1973, pp. 0–8. (To have been presented Int. Conf. and Instruments Exhibition in Particle Technology, Chicago, Ill., Aug. 1973).

Water Associates brochure, "Waters HPLC Automation System", Sep. 1981, pp. 1–18.

Verillon et al., "Automatic Liquid Sample Processor for Large Series of Complex Analyses", American Laboratory, Oct. 1987, pp. 88–95 (entire article).

Direct Scientific brochure, "Peristaltic, Electronically Controlled Pump and Robotic Vial, Tube, Bottle Filler," Spring 1987, pp. 1–4.

Rainin Instrument Co. brochure, "HPLC Autosampler Model K65B", Apr. 1986, PB-25, pp. 1–4.

E. Merck brochure, "The 655A-40 Autosampler", 22/II 211605, 6/10/985R, pp. 1–4 (pub. by Jul. 1988).

EM Science brochure, "The World of Em Science/Hitachi Presents the Model 655 A-40 Autosampler for HPLC," 1985, pp. 1∝4.

Dahnke, "Automated Nitrogen Pore Volume Distribution Instrument," Jul. 30, 1980, pp. i-iv, 1–21, (to have been presented at 1981 Pittsburgh Conf. on Analytical Chemistry & Applied Spectroscopy).

Quantachrome Corp. brochure, "Microscane Particle Size Analyzer," pp. 759–766, pub. by Jul. 1988.

Quantachrome Corp. Owner's Manual, "Microscan Particle Size Analyzer", 6/86.

Micromeritics Instrument Corp. brochure, "Sedigraph 5000ET," 4/86, Form 501/42703/00, pp. 00092–00096, 00099.

Micromeritics Instrument Corporation brochure "Sedigraph 5000D Particle Size Analyzer" Form 500/42703/00, pp. 00414–00421, pub. by Jul. 1988.

Micromeritics Instrument Corp. "Instrument Manual Sedigraph 5000 ET Particle Size Analyzer", Jan. 15, 1986, pp. 00001–000089.

Micromeritics Instrument brochure "725 Auto Injector," 6/80 Form 725/42701/00, pp. 1–4.

Fig_1

Fig_8

AUTOMATIC SAMPLE FEEDER FOR SUSPENDED SAMPLES

CROSS REFERENCE TO RELATED APPLICATION

This application is a continuation-in-part of U.S. Application Ser. No. 125,395, filed Nov. 25, 1987, entitled "X-RAY PARTICLE SIZE ANALYZER."

TECHNICAL FIELD

The present invention relates to devices for sequentially feeding samples to an analyzer for testing, and more particularly relates to an apparatus and method for sequentially preparing and feeding suspensions of finely divided material to an analyzer such as a particle size analyzer.

BACKGROUND ART

In the laboratory, it is often necessary to carry out a particular type of analysis on a large number of similar samples. Thus, it has long been a goal in designing laboratory instrumentation to automate testing as much as possible and to minimize human participation and supervision.

One approach to handling multiple samples has been to equip the analyzer with multiple analysis stations. A static volume adsorption surface area analyzer using this technique is shown in U.S. Pat. No. 4,566,326. Another approach has been to conduct analysis within a container, such as a vial or beaker, and to move the containers sequentially to an analysis station which analyzes the sample within the container. An optical density plasma analyzer using this technique is shown in U.S. Pat. No. 3,607,099.

A third approach to handling multiple samples has been to withdraw samples from multiple storage containers and to inject them into the analyzer mechanism sequentially. This approach has been successfully utilized when the sample is in solution in a carrier liquid, such that the solution can be left unattended for long periods and always be ready for withdrawal, injection, and analysis. U.S. Pat. Nos. 3,918,913 and 4,622,457 show autosamplers for liquid chromatographs. The autosamplers of these patents carry multiple sample vials on turntables which allow the vials to be indexed individually with respect to a needle injection mechanism which withdraws the sample. Other autosamplers have used an indexing mechanism for moving a sample withdrawal mechanism over an array of sample vials to obtain samples in a programmed sequence.

Generally, mechanisms of the type described permit flushing of the interior of the sampling lines to wash out the previous sample before exposure to a new sample. For example, the automatic sampler mechanism shown in U.S. Pat. No 4,478,095 has a flush solvent mechanism which is associated with the sampling needle syringe so that flush solvent and not sample is always in the syringe. Exterior washing of the sampling needle has also been provided in similar systems.

Although the above autosampling systems have worked well handling solutions, particular problems associated with suspensions of fine powders have prevented the use of similar devices in connection with sedimentation particle size analyzers and other systems which analyze suspensions. Measuring particle size distributions accurately requires that in a representative sample each and every grain be separated from all others so that the contribution of all grains can be assessed.

Dispersing the particles of a powder is most reliably accomplished by mixing the powder in a liquid. Often, surfactants and wetting agents must be added, and the liquid vigorously agitated. Once complete suspension of the particles is accomplished, this state must be maintained up to the start of sedimentation to obtain accurate results.

Studies have concluded that ultrasonic treatment with simultaneous stirring produces an acceptable dispersion of many powders in typical dispersing liquids. One practice in preparing samples for particle size analysis has been initially to place a beaker containing the sample and liquid onto an elevator which raises the beaker to immerse an ultrasonic probe into the liquid. The ultrasonic vibrations assist in breaking up agglomerations of the particles. Then the particles have been dispersed by inserting a rotating stirring blade or by recirculating the mixture with a pump after positioning the beaker into the analyzer. By handling the sample beakers individually and using them as the sample reservoir in the analyzer, it has been assured that the concentration of particles is correct for analysis and that no agglomerations of particles are present.

Thus, conventional procedures for supplying suspended samples to analyzers require a great deal of operator involvement. The autosampler concept has not been used because samples left in a tray for extended periods can settle out of suspension and even reagglomerate. Sedimentation particle size analysis may take from about ten minutes to over one hour depending on the degree of detail desired. Therefore, the last samples transferred by a feeder might have been left unattended for several hours.

Thus a major problem with adapting a conventional autosampling device for suspensions would be that the device could not establish complete suspension of the sample prior to transfer to the analyzer. Nor could it assure that an acceptable concentration of sample per volume of dispersing liquid would be transferred following a period of settling in the beaker. Thus, there has been a need in the art for a sequential sample feeder for suspended samples with the ability to assure that the samples are fully suspended at the time of transfer to the analyzer.

SUMMARY OF THE INVENTION

The present invention solves the above problems in the art by providing an automatic sample feeder that can reliably deliver suspended samples to an analyzer. This is accomplished by providing a system for assuring that the sample is suspended in a dispersing liquid at the time the sample is transferred to the analyzer.

Generally described, the present invention provides an apparatus and method for feeding suspended particulate samples to an analyzer according to which a plurality of samples are stored in containers in dispersing liquid, the samples are sequentially delivered to the analyzer, and the samples are maintained in suspension in the dispersing liquid when the samples are delivered to the analyzer.

More particularly described, the sample feeding apparatus can include a plurality of sample containers for storing particulate samples and liquid in which each particulate sample is to be suspended; and sample preparation and delivery means responsive to a first signal from the analyzer for suspending a first sample in a first one of the containers in the liquid and for delivering a volume of the first sample from the first container to the analyzer while the first sample is being maintained in suspension, and responsive to a second signal from the analyzer for suspending a second sample in a second one of the containers in the liquid and for delivering a volume of the second sample from the second container to the analyzer while the second sample is being maintained in suspension.

The sample preparation and delivery means preferably comprises an assembly for agitating and withdrawing the sample, the assembly being dimensioned to fit into the containers; and means for inserting and withdrawing the assembly from the containers responsive to the signals from the analyzer. The sample agitation and withdrawal assembly can include a stirring blade, an ultrasonic probe, and a fluid delivery line. An apparatus can be provided to move the assembly and the plurality of containers relative to one another and to insert the stirring blade, ultrasonic probe and delivery line into the containers responsive to the signals from the analyzer.

The invention also preferably provides a means for cleaning one sample from the sample preparation and delivery means prior to contact with the next sample. This my be accomplished by directing fluid back through the delivery line onto the rotating stirrer blade, which effectively sprays the fluid onto the surrounding components to rinse them. The fluid also flushes the interior of the line before hitting the stirrer blade. This cleaning system may be utilized in connection with dissolved samples as well as suspended samples.

The invention also provides a method of delivering suspended particulate samples to an analyzer, comprising the steps of placing the samples and a suspending liquid into a plurality of sample containers; responsive to a first signal from the analyzer, suspending a first sample in a first one of the containers in the liquid, and delivering the suspended first sample to the analyzer; and, responsive to a second signal from the analyzer, suspending a second sample in a second one of the containers in the liquid, and delivering the suspended second sample to the analyzer. The step of suspending the sample comprises agitating the sample in the liquid with ultrasonic vibrations emanating from an ultrasonic probe and with a stirring element. The method may include a rinsing step of scattering fluid directed into the container with the stirring element.

Thus, it is an object of the present invention to provide an automatic feeder apparatus and method for an analyzer requiring suspended samples.

It is a further object of the present invention to provide an automatic feeder system capable of maintaining a sample in suspension at the time the sample is delivered to an analyzer.

It is a further object of the present invention to provide an automatic feeder system capable of consistently delivering an acceptable concentration of a suspended sample to an analyzer.

It is a further object of the present invention to provide an automatic feeder system for delivering samples sequentially to an analyzer without contamination of a subsequent sample by a previous sample.

It is a further object of the present invention to provide an automatic feeder system for suspensions of particles which can disperse the particles without need for preliminary sample preparation.

It is a further object of the present invention to provide a sequential sample feeder system adapted for use with a sedimentation particle size analyzer.

Other objects, features, and advantages of the present invention will become apparent upon reading the following detailed description of embodiments of the invention, when taken in conjunction with the accompanying drawing and the appended claims. BRIEF DESCRIPTION OF THE DRAWING

FIG. 1 shows an automatic sample feeding apparatus 10, which can be interconnected to deliver samples to an analyzer in the manner shown in FIG. 6. Generally described, the feeding apparatus 10 includes a rotatable tray 12 on which are carried an array of beakers 14 containing various samples to be analyzed, and a sample preparation and delivery assembly 15 which sequentially prepares and extracts the samples and sends them to a mixing vessel 17 of an analyzer, such as a sedimentation particle size analyzer. The sequence of operation of the feeding apparatus 10 is controlled by a feeder computer 20, which communicates with an analyzer computer 22 for coordination of sample feeding with the analysis of samples by the analyzer. The present invention is particularly suitable for use with an x-ray particle size analyzer of the type disclosed in U.S. Application Ser. No. 125,395, which is incorporated herein by reference in its entirety.

Figure 1:
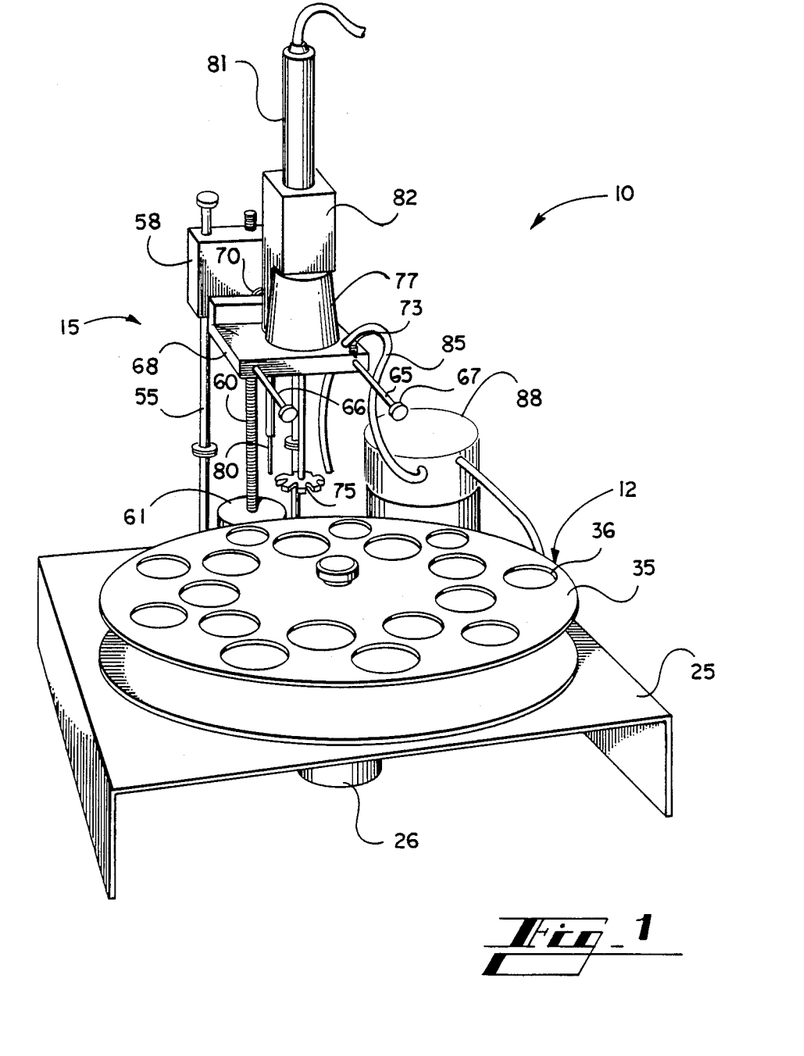
FIG. 1 is a pictorial view of an automatic sample feeding apparatus embodying the present invention.
Figures 2, 5:
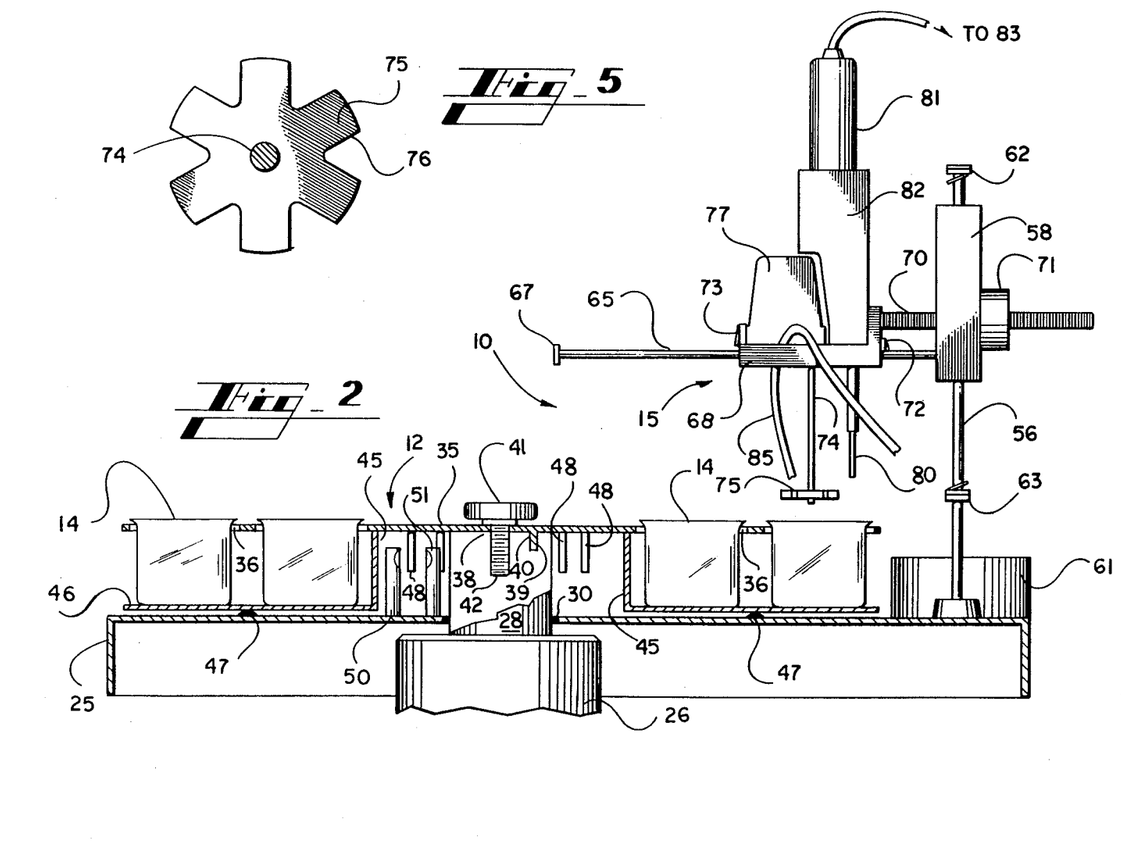
FIG. 2 is a side view of the apparatus of FIG. 1, showing the rotatable tray and base in cross section.
FIG. 5 is a bottom plan view of the stirrer blade.
Figures 3, 4:
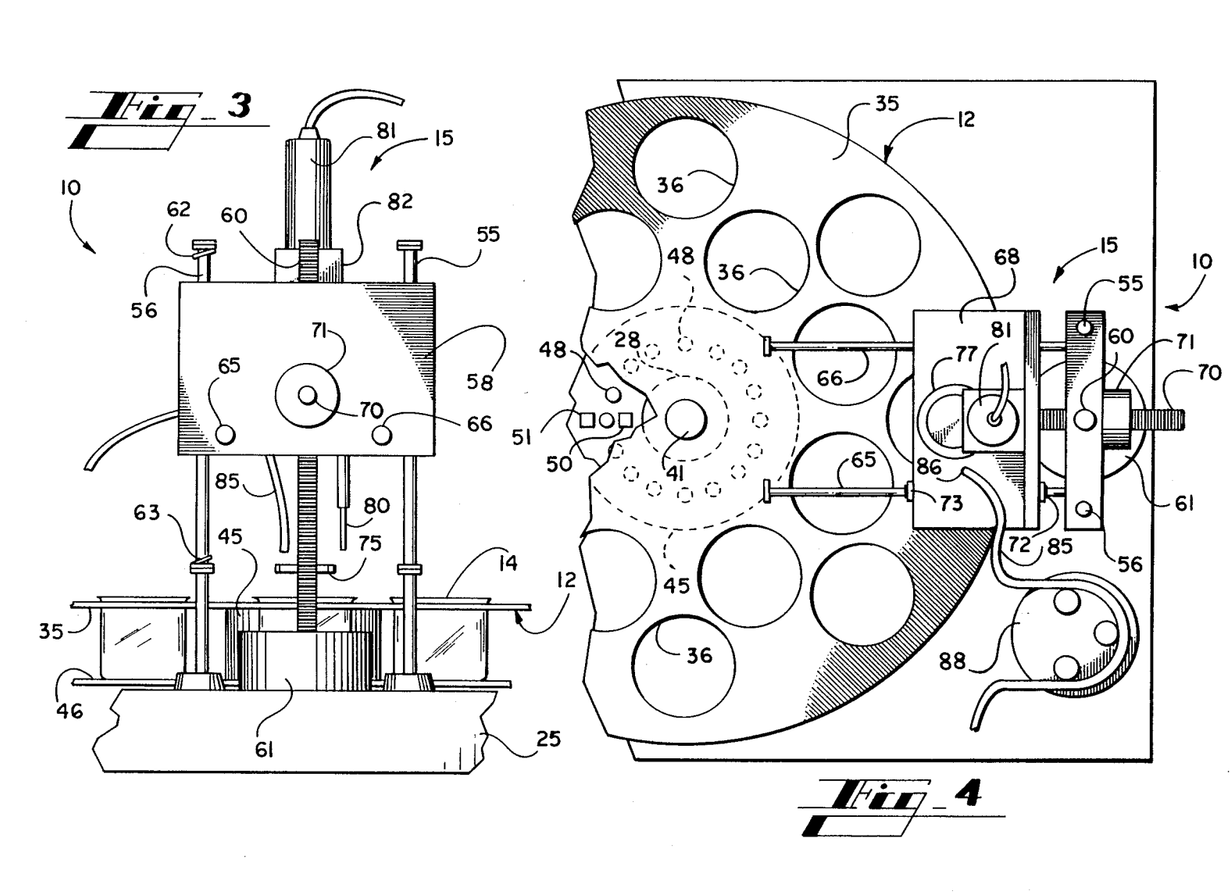
FIG. 3 is a rear view of the sample preparation and delivery assembly.
FIG. 4 is a partial top view of the apparatus of FIG. 1.

As shown in FIGS. 1, 2 and 4, the rotatable tray 12 is mounted for rotation on a base 25. A tray drive motor 26 is positioned under the center of the base 25. A cylindrical drive member 28 is drivingly connected to the motor 26, and projects through an opening in the base defined by a circular sealing gasket 30. The tray 12 includes a top plate 35, which defines a plurality of beaker openings 36, preferably arranged in two concentric circles of nine openings each. A small central opening 38 is defined in the top plate 35, and a locator pin 39 extends downwardly from the underside of the plate 35 adjacent to the opening 38.

When the tray 12 is placed on the base 25, the top plate 35 rests on the cylindrical drive member 28. The locator pin 39 is inserted into a locator bore 40 in the drive member 28, and a lock nut 41 having an enlarged knob is inserted through the opening 38 into a threaded opening 42 defined in the center of the drive member 28. Together, the lock nut 41 and locator pin 39 assure that the tray 12 is always positioned in the same orientation with respect to the drive member 28. This allows the sample preparation and delivery assembly 15 to find any of the beaker openings in the manner described below.

The rotatable tray 12 further includes a cylindrical wall 45 extending downwardly from the top plate 35 just inside the inner circle of beaker openings. An annular bottom plate 46 is attached to the bottom of the cylindrical wall 45 and extends under the beakers 14. A plurality of bearings 47, preferably buttons made of Nylon, Teflon, or the like, are attached to the base 25 under the bottom plate 46. The bearings 47 reduce friction as the tray 12 is rotated over the base 25 by the drive member 28.

Also projecting downwardly from the top plate 35 of the tray 12 are a plurality of pins 48, forming a circle in the space between the cylindrical wall 45 and the drive member 28. Each pin 48 is aligned radially with one of the beaker openings 36 in the top tray. The pins pass between a photocell transmitter (or transmitter/receiver) 50 and a photocell receiver (or reflector) 51, which are both mounted on the base 25 within the cylindrical wall 45. The photocell components 50 and 51 are connected to the feeder computer 20 and provide information relating to the position of the tray 12.

The sample preparation and delivery assembly 15 is shown in FIGS. 1-4. A pair of vertical guide rods 55 and 56 are mounted to the base 25 adjacent to the periphery of the tray 12. An elevator block 58 is slidably mounted on the guide rods for vertical movement, which is accomplished by a drive screw 60 that is vertically threaded through the elevator block 58. A reversible vertical drive motor 61 positioned on the base between the guide rods 55 and 56 is drivingly connected to the drive screw 60 so as to cause the drive screw 60 to rotate, which in turn causes the elevator block 58 to move up or down the drive screw. The travel of the elevator block 58 is restricted by an upper limit switch 62 and a lower limit switch 63, both mounted on the guide rod 56. Upon engagement of either switch 62 or 63 by the elevator block, a signal is provided to the feeder computer 20, which shuts down the motor 61.

A pair of horizontal guide rods 65 and 66 extend from the elevator block 58 toward the center of the tray 12, as best shown in FIG. 4. The horizontal guide rods terminate at a position inside the inner circle of beaker openings 36. A movable platform 68 is slidably mounted on the horizontal guide rods. The platform 68 is moved by a horizontal drive screw 70 that is fixedly attached to the platform. The drive screw 70 passes through an opening in the elevator block and is threaded through a drive nut (not shown) associated with a horizontal drive motor 71 mounted on the elevator block 58. When the motor 71 operates, the drive nut revolves in conventional fashion and causes the drive screw 70 to be drawn through the motor 71 in either direction, thereby moving the platform 68.

Movement of the platform 68 is restricted by an outer limit switch 72 and an inner limit switch 73, which may be mounted on the outer and inner edges of the platform 68. When the platform reaches the elevator block in its outward travel or a stop 67 at the end of the guide rod 65, the appropriate limit switch is engaged, and a signal is provided to the feeder computer 20, which shuts down the motor 71.

As best shown in FIG. 2, a shaft 74 extends downwardly from the platform 68 and terminates in a horizontally orientated stirrer blade 75. The length of the shaft 74 is selected so that the blade 75 is above the top of the beakers 14 when the elevator block is raised to its uppermost position, and so that the blade can be lowered near the bottom of the beakers. The shape of the stirrer blade 75 is shown in FIG. 5. The blade has a generally circular periphery interrupted by several cutouts 76 extending about half the radius of the blade toward the center of the blade. A stirrer motor 77 is mounted on the platform 68. The shaft 74 extends through an opening in the platform 68 and is rotated by the motor 77, to which the shaft is drivingly connected.

Also extending downwardly through an opening in the platform 68 is an ultrasonic probe 80. The probe 80 is positioned adjacent to the shaft 74 and terminates slightly above the stirrer blade 75. The vibrating probe 80 is driven by an ultrasonic driver 81 supported by a housing 82 which is mounted on the platform 68. A conventional ultrasound controller 83, shown diagrammatically in FIG. 7, is utilized to operate the probe 80.

The final element of the sample preparation and delivery assembly 15 is a dip tube or fluid delivery line 85. The tube 85 may be formed of suitable plastic or other material. It is passed from the top of the platform 68 through an opening 86, and extends downwardly alongside the stirrer shaft 74. The fluid tube terminates above the stirrer blade 75, such that fluid pumped through the tube 85 into a beaker will strike the stirrer blade 75.

Figure 6:
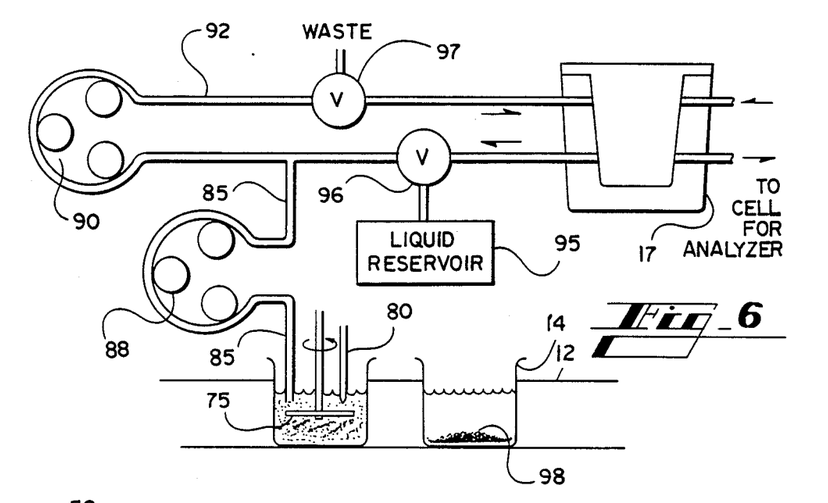
FIG. 6 is a schematic diagram showing the interconnection of the sample preparation and delivery assembly with a particle size analyzer.

A reversible peristaltic feeder pump 88 is mounted on the base 25 adjacent to the sample preparation and delivery assembly 15. The delivery tube 85 passes through the pump 88 and extends to a connection with the mixing assembly of the particle size analyzer, as shown in FIG. 6 and described below.

Figure 7:
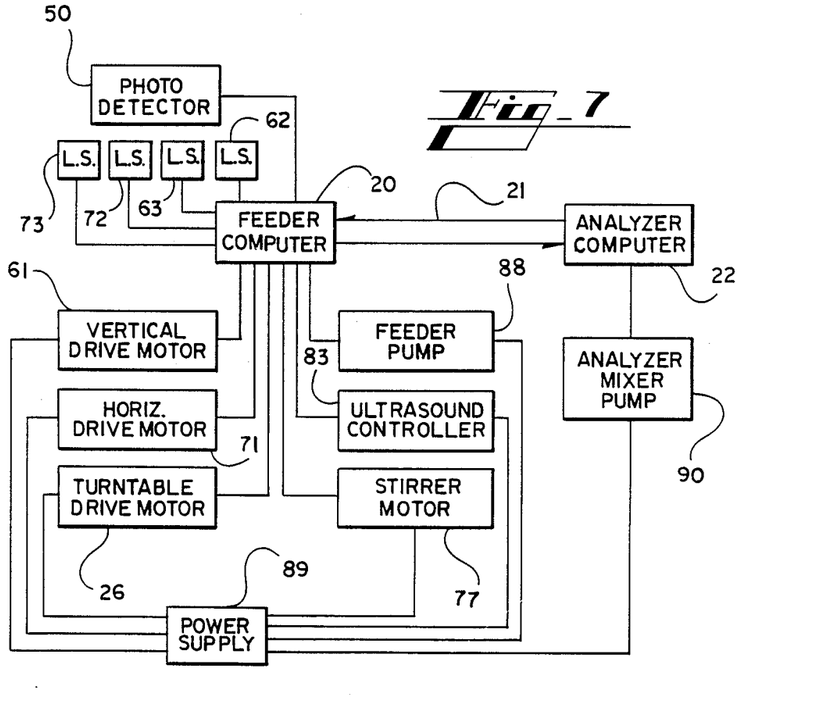
FIG. 7 is a schematic diagram of the electrical control circuit for the sample feeding apparatus.

An electrical circuit for controlling the automatic feeding apparatus 10 is shown in FIG. 7. The feeder computer 20 includes a programmable microprocessor that can be programmed by a programmer of ordinary skill in the art to carry out the functions and steps described herein. Through a conventional interface 21, the feeder computer 20 can communicate with and be controlled by the analyzer computer 22. The feeder computer receives input signals from the limit switches 62, 63, 72, and 73, and from the photodetector 50,51. Control signals are transmitted from the computer 20 to the vertical drive motor 61, the horizontal drive motor 71, the turntable motor 26, the stirrer motor 77, the ultrasound controller 83, and the feeder pump 88. The latter components also are connected to a conventional power supply 89.

The liquid interface noted above between the feeding apparatus 10 and the analyzer is accomplished by connecting the delivery tube 85 to a tube 92 which recirculates liquid and/or suspended sample contained in the mixing chamber 17 of the analyzer. A peristaltic mixing pump 90 is located along the tube 92, which also includes a liquid supply valve 96 upstream of the pump 90 operable to connect the tube 92 to a supply of clear liquid from a reservoir 95, and a waste valve 97 operable to direct flow through the tube 92 to waste. These components and their operation are described in detail in the above-referenced Application Ser. No. 125,395. The junction of the tube 85 with the tube 92 is between the pump 90 and the supply valve 96, and need not be valved because the pump 90 can act as a valve as described below.

Figure 8:
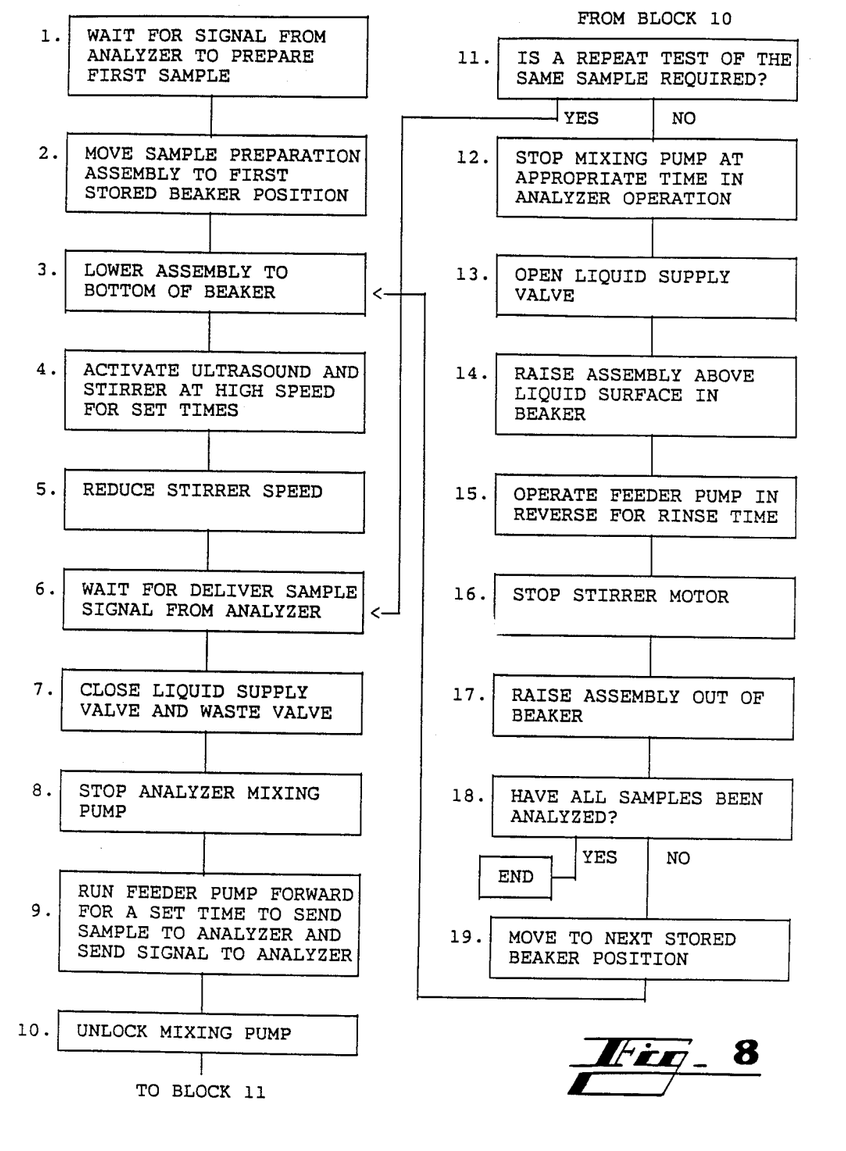
FIG. 8 is a schematic flow chart of the operation of the sample feeding apparatus. DETAILED DESCRIPTION Referring now in more detail to the drawing, in which like numerals refer to like parts throughout the several views.

Operation of the automatic feeder apparatus 10 under the control of the computers 20 and 22 is carried out according to a sequence shown diagrammatically in FIG. 8. Prior to the initiation of operation, a plurality of samples 98 are placed with a dispersing liquid into a plurality of beakers 14. The beakers 14 are then placed into the openings 36 in the tray 12, and information identifying the sample and its location in the tray 12 is input into data storage associated with the analyzer computer 22. Information relating to the duration of ultrasonic treatment and high speed stirring may also be entered for each sample. Operation of the ultrasound probe may be omitted entirely if not required to suspend the particular sample. The tray 12 is placed onto the drive member 28 with the locator pin 39 in the locator opening 40, and the motor 26 is reset to place the drive member 28 in a known starting orientation.

Referring to FIG. 8, at the beginning of a series of sample analyses, the analyzer computer sends a signal to the feeder computer requesting preparation of a particular sample. The feeder computer operates the tray drive motor 26 to position the beaker opening 36 in which the sample has been placed in radial alignment with the path of horizontal travel of the platform 68. Rotational indexing of the tray 12 is accomplished by counting the pins 48 which pass the photodetector 50,51 as the tray 12 moves. The computer also operates the horizontal drive motor 71 to extend or retract the platform 68 until the sample preparation and delivery assembly is positioned directly above the desired beaker 14. The vertical drive motor 61 is then operated to lower the stirrer blade 75, ultrasonic probe 80, and delivery tube 85 below the surface of liquid in the beaker, as noted in Block 3 of FIG. 8.

At this time the ultrasonic probe 80 is operated for a selected time, such as 2–3 minutes, to break up agglomerations of the sample particles. Simultaneously, the stirrer motor 77 is operated at high speed to vigorously agitate the sample within the dispersing liquid. After 1–2 minutes, the stirrer speed may be reduced to a moderate speed adequate to maintain the sample in suspension. The times of operation of the probe 80 and the stirrer 75 may be made programmable from the console of the analyzer computer 22, to permit adjustment depending upon the requirements of each sample.

As noted in Blocks 6–8 of FIG. 8, when the analyzer mixing chamber 17 is ready for the new suspended sample, the mixing pump 90 is stopped, the valves 96 and 97 are closed, and a signal is transmitted from the computer 22 to the computer 20 to request delivery of the sample. The feeder pump 88 is then operated in a forward direction to withdraw suspended sample from the beaker 14 and pump the sample along the tube 85, into and along the tube 92 in the upstream direction opposite to flow caused by the pump 90, through the valve 96, and into the mixing vessel 17. The rollers of the mixing pump 90 occlude the tube 92 and therefore prevent any of the suspension from entering the downstream leg of the tube 92.

The pump 88 is operated for a set time sufficient to pump a known volume of suspension to the mixing vessel, based upon the known characteristics of the pump 88. After delivery of the sample suspension, the pump 88 is stopped and the mixing pump 90 is unlocked to enable it to perform its normal function in maintaining the sample in suspension in the mixing vessel. A signal is sent to the analyzer computer 22 that transfer of the sample is complete.

Referring now to Block 11 of FIG. 8, the computer memory is checked to determine whether the data input for the sample just transferred includes a request for a repeat analysis. If so, the sequence returns to Block 6. When another ready signal is received from the analyzer computer 22, the pump 90 is stopped, the valves are closed, and the transfer proceeds as described above. It should be noted that the stirrer has continued to operate within the beaker at a moderate speed to maintain the sample in suspension.

If no repeat analysis has been requested, the sequence of operation proceeds to Block 12–15, according to which the delivery tube is flushed and the components that have been lowered into the beaker are rinsed to minimize contamination of the next sample. First, the mixing pump 90 is again stopped at an appropriate time during normal operation of the analyzer to block the tube 92. Then the liquid supply valve 96 is opened to the reservoir 95. The platform 68 is raised by operation of the motor 61 until the stirrer blade is above the surface of the liquid in the beaker, but still within the walls of the beaker. At the same time the feeder pump 88 is operated in reverse to draw clear liquid from the reservoir 95 through the tube 92, into the tube 85, and to direct a stream of liquid onto the still rotating stirrer blade 75. The blade breaks up the incoming stream of liquid and flings droplets onto the components within the beaker, effectively rinsing off most of the suspension clinging to them.

It is not necessary to rinse off all of the prior sample since it has been shown that the rinsing process just described results in only about 0.1% contamination of the next sample. This is not significant, because the x-ray detection system used in sedimentation particle size analyzers is only accurate to plus or minus 0.25%.

After the pump has operated in reverse to supply about 50 ml of rinsing liquid back into the beaker, the stirrer motor 77 is stopped, and the motor 61 is operated to raise the stirrer blade, delivery tube, and ultrasonic probe completely out of the beaker. If there are more samples to be transferred for analysis, the motors 26 and 71 are again operated to position the sample preparation and delivery assembly 15 over the next sample beaker 14 in the sequence stored in the computer memory, as noted in Block 19 of FIG. 8. The operational sequence returns to Block 3 of FIG. 8, and the motor 61 is operated to lower the assembly into the beaker. Operation then continues as described above until all the samples identified in the computer memory have been analyzed.

As described in Application Ser. No. 125,395, the particle size analyzer conducts tests prior to each run to assure that the sample in the test cell has the correct concentration, is fully suspended, and is free of bubbles. If enough time is available for preparation of the next sample during the x-ray scanning of the sample in the analyzer, it would be possible to program the computers to delay moving the sample preparation and delivery assembly to the next sample beaker until the above-described tests were performed. If the suspension was rejected by the analyzer, the ultrasonic probe and stirrer could be operated again to attempt to overcome any problem with agglomeration of the sample, and a new supply of the sample could be delivered to the mixing vessel 17.

It will be understood by those skilled in the art that the disclosed embodiment could be modified so that, rather than initially dispersing the sample just before transfer to the analyzer, the device could receive an already dispersed sample and either maintain it in suspension or re-disperse it prior to transfer, and still be within the broad concept of the present invention.

From the foregoing it will be understood that the present invention provides an automatic sample feeder system capable of maintaining a sample in suspension at the time of delivery of the sample to an analyzer. The system is also capable of dispersing a particulate sample into suspension without preliminary sample preparation, consistently delivering an acceptable concentration of a suspended sample, and cleaning and flushing its components between samples to avoid contamination.

While this invention has been described in detail with particular reference to preferred embodiments thereof, it will be understood that variations and modifications can be effected within the spirit and scope of the invention as described hereinbefore and as defined in the appended claims.

We claim:

1. An apparatus for feeding particulate samples to an analyzer, comprising:
    a plurality of sample containers for storing particulate samples and liquid in which said particulate is to be suspended; and
    sample preparation and delivery means responsive to a first signal from said analyzer for suspending a first sample in a first one of said containers in said liquid and for removing a volume of said first sample from said first container and delivering said volume of said first sample to said analyzer while said first sample is being maintained in suspension in said first sample container, and responsive to a second signal from said analyzer for suspending a second sample in a second one of said containers in said liquid and for removing a volume of said second sample from said second container and delivering said volume of said second sample to said analyzer while said second sample is being maintained in suspension in said second sample container.

2. The apparatus of claim 1, wherein said sample preparation and delivery means further comprises means for cleaning said first sample from said sample preparation and delivery means prior to contact with said second sample.

3. The apparatus of claim 1, wherein said sample preparation and delivery means comprises an assembly of means for agitating and withdrawing said sample, said assembly being dimensioned to fit into said containers; and means for inserting and withdrawing said assembly from said containers responsive to said signals from said analyzer.

4. The apparatus of claim 1, wherein said sample preparation and delivery means includes:
    a sample preparation and delivery assembly including a stirring blade, an ultrasonic probe, and a fluid delivery line; and
    means for moving said sample preparation and delivery assembly and said plurality of containers relative to one another for inserting said stirring blade, ultrasonic probe and delivery line into said containers responsive to said signals from said analyzer.

5. The apparatus of claim 4, wherein said stirring blade, ultrasonic probe and delivery line are mounted on a common, movable frame.

6. The apparatus of claim 5, wherein said containers are mounted on a movable tray, and further comprising means for moving said tray to place a selected container under said movable frame.

7. The apparatus of claim 4, wherein said delivery line is mounted above said stirring blade, and further comprising means associated with said delivery line for selectively directing clear liquid onto said stirring blade while said blade is rotating, whereby said clear liquid is scattered about said container, rinsing said stirring blade, ultrasonic probe and delivery line.

8. A method of providing particulate samples to an analyzer, comprising the steps of:
    placing said samples and a suspending liquid into a plurality of sample containers;
    responsive to a first signal from said analyzer, suspending a first sample in a first one of said containers in said liquid;
    maintaining the first sample in uniform suspension;
    removing a volume of said suspended first sample from said first container and delivering said suspended first sample to said analyzer;
    responsive to a second signal from said analyzer, suspending a second sample in a second one of said containers in said liquid;
    maintaining the second sample in uniform suspension; and
    removing a volume of said suspended second sample from said second container and delivering said suspended second sample to said analyzer.

9. The method of claim 8, wherein said steps of suspending said sample comprises agitating said sample in said liquid with ultrasonic vibrations emanating from an ultrasonic probe and with a stirring element.

10. The method of claim 9, further comprising rinsing said stirring element and ultrasonic probe with said liquid prior to suspending said second sample.

11. The method of claim 10, wherein said step of rinsing said stirring element and ultrasonic probe comprises directing clear liquid through a fluid line into said first sample container while said stirring element and ultrasonic probe are positioned within said first sample container and while said stirring element is rotating.

12. The method of claim 11, wherein said rinsing step includes scattering the liquid directed into said container through said fluid line with said stirring element.

13. The method of claim 9, wherein said steps of suspending and delivering said sample each comprise inserting said ultrasonic probe, said stirring element and a fluid line into said first or second sample container, agitating said sample with said probe and said stirring element, and withdrawing said sample through said fluid line.

14. An apparatus for feeding particulate samples to an analyzer, comprising:
    a plurality of sample containers for storing said sample in dispersing liquid;
    means for sequentially delivering each of said samples to said analyzer; and
    means for maintaining said samples in suspension in said dispersing liquid when said samples are delivered to said analyzer.

15. The apparatus of claim 14, wherein said means for maintaining said samples in suspension when said samples are delivered comprises means for inserting an ultrasonic probe and a stirring element into the one of said containers from which a sample is about to be delivered to said analyzer.

16. A sample preparation and delivery apparatus for delivering a sample to an analyzer, comprising:
    a container of said sample;
    a stirring blade;
    a fluid delivery line positioned above said stirring blade; and
    means associated with said delivery line for selectively directing clear liquid onto said stirring blade, whereby said liquid is scattered about said container, rinsing said stirring blade and delivery line.

* * * * *